United States Patent
Lee

(10) Patent No.: US 9,095,712 B2
(45) Date of Patent: Aug. 4, 2015

(54) ELECTRICAL STIMULATION METHOD FOR MODULATION ON SENSORY INFORMATION AROUND DORSAL ROOT GANGLIA

(71) Applicant: BOSTON SCIENTIFIC NEUROMODULATION CORPORATION, Valencia, CA (US)

(72) Inventor: Dongchul Lee, Agua Dulce, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/904,891

(22) Filed: May 29, 2013

(65) Prior Publication Data
US 2013/0325084 A1    Dec. 5, 2013

Related U.S. Application Data

(60) Provisional application No. 61/652,838, filed on May 29, 2012.

(51) Int. Cl.
*A61N 1/36* (2006.01)
*A61N 1/372* (2006.01)

(52) U.S. Cl.
CPC ........ *A61N 1/36071* (2013.01); *A61N 1/36185* (2013.01); *A61N 1/36057* (2013.01); *A61N 1/36171* (2013.01); *A61N 1/37241* (2013.01); *A61N 1/37247* (2013.01)

(58) Field of Classification Search
CPC ........... A61N 1/36071; A61N 1/37235; A61N 1/37247; A61N 1/0551; A61N 1/36139; A61N 1/36171; A61N 1/36021; A61N 1/36185; A61N 1/3787

USPC ........................................ 607/1–3, 46–48, 59
See application file for complete search history.

(56) References Cited

U.S. PATENT DOCUMENTS

| | | |
|---|---|---|
| 6,516,227 B1 | 2/2003 | Meadows et al. |
| 6,895,280 B2 | 5/2005 | Meadows et al. |
| 6,993,384 B2 | 1/2006 | Bradley et al. |
| 7,539,538 B2 | 5/2009 | Parramon et al. |
| 8,718,790 B2 | 5/2014 | Pianca |
| 8,768,488 B2 | 7/2014 | Barker |
| 2003/0139781 A1 | 7/2003 | Bradley et al. |
| 2005/0267546 A1 | 12/2005 | Parramon et al. |
| 2010/0010566 A1 | 1/2010 | Thacker et al. |
| 2010/0121409 A1 | 5/2010 | Kothandaraman et al. |
| 2012/0046715 A1 | 2/2012 | Moffitt et al. |
| 2012/0310140 A1* | 12/2012 | Kramer et al. ............. 604/20 |
| 2013/0304152 A1 | 11/2013 | Bradley et al. |

(Continued)

FOREIGN PATENT DOCUMENTS

| | | |
|---|---|---|
| WO | 2013177145 | 11/2013 |
| WO | 2013177159 | 11/2013 |

(Continued)

*Primary Examiner* — Rex R Holmes
(74) *Attorney, Agent, or Firm* — Lowe Graham Jones PLLC; Bruce E. Black

(57) ABSTRACT

A method of treating a patient with an ailment, comprises delivering first energy to a dorsal root ganglia (DRG), thereby modulating the DRG, and delivering second energy to at least one of a central neural axon extending from the DRG and a peripheral neural axon extending from the DRG, thereby modulating the at least one of the central neural axon and the peripheral neural axon.

20 Claims, 11 Drawing Sheets

(56) References Cited

U.S. PATENT DOCUMENTS

| | | |
|---|---|---|
| 2013/0317518 A1 | 11/2013 | Govea |
| 2013/0317572 A1 | 11/2013 | Zhu et al. |
| 2013/0317573 A1 | 11/2013 | Zhu et al. |
| 2013/0317583 A1 | 11/2013 | Pianca |
| 2013/0317585 A1 | 11/2013 | Barker |
| 2013/0317586 A1 | 11/2013 | Pianca |
| 2013/0317587 A1 | 11/2013 | Barker |
| 2013/0317588 A1 | 11/2013 | Howard et al. |

FOREIGN PATENT DOCUMENTS

| | | |
|---|---|---|
| WO | 2013177307 | 11/2013 |
| WO | 2013177312 | 11/2013 |

* cited by examiner

G2: Cell body modulation
G1: Peripheral axon modulation

G1: Cell body modulation
G2: Central axon modulation

G1: Central axon modulation
G2: Cell body modulation
G3: Peripheral axon modulation

ELECTRICAL STIMULATION METHOD FOR MODULATION ON SENSORY INFORMATION AROUND DORSAL ROOT GANGLIA

RELATED APPLICATION DATA

The present application claims the benefit under 35 U.S.C. §119 to U.S. provisional patent application Ser. No. 61/652,838, filed May 29, 2012. The foregoing application is hereby incorporated by reference into the present application in its entirety.

FIELD OF THE INVENTION

The present invention relates to tissue modulation systems, and more particularly, to a system and method for therapeutically modulating nerve fibers.

BACKGROUND OF THE INVENTION

Among many techniques attempted for neurostimulation (e.g., electrical, chemical, mechanical, thermal, magnetic, optical, and so forth), electrical stimulation is the standard and most common technique. Implantable electrical stimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) techniques, which directly stimulate the spinal cord tissue of the patient, have long been accepted as a therapeutic modality for the treatment of chronic pain syndromes, and the application of spinal cord stimulation has begun to expand to additional applications, such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems such as the Freehand system by NeuroControl (Cleveland, Ohio) have been applied to restore some functionality to paralyzed extremities in spinal cord injury patients. Occipital Nerve Stimulation (ONS), in which leads are implanted in the tissue over the occipital nerves, has shown promise as a treatment for various headaches, including migraine headaches, cluster headaches, and cervicogenic headaches. In recent investigations, Peripheral Stimulation (PS), which includes Peripheral Nerve Field Stimulation (PNFS) techniques that stimulate nerve tissue directly at the symptomatic site of the disease or disorder (e.g., at the source of pain), and Peripheral Nerve Stimulation (PNS) techniques that directly stimulate bundles of peripheral nerves that may not necessarily be at the symptomatic site of the disease or disorder, has demonstrated efficacy in the treatment of chronic pain syndromes and incontinence, and a number of additional applications are currently under investigation. Vagal Nerve Stimulation (VNS), which directly stimulates the Vagal Nerve, has been shown to treat heart failure, obesity, asthma, diabetes, and constipation.

Each of these implantable stimulation systems typically includes at least one stimulation lead implanted at the desired stimulation site and neurostimulator (e.g., an implantable pulse generator (IPG)) implanted remotely from the stimulation site, but coupled either directly to the electrode lead(s) or indirectly to the stimulation lead(s) via a lead extension. Thus, electrical pulses can be delivered from the neurostimulator to the stimulation lead(s) to stimulate or activate a volume of neural tissue. In particular, electrical energy conveyed between at least one cathodic electrode and at least one anodic electrode creates an electrical field, which when strong enough, depolarizes (or "stimulates") the neurons beyond a threshold level, thereby inducing the firing of action potentials (APs) that propagate along the neural fibers. The stimulation regimen will typically be one that provides stimulation energy to all of the target tissue that must be stimulated in order to provide the therapeutic benefit, yet minimizes the volume of non-target tissue that is stimulated.

The stimulation system may further comprise a handheld remote control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon. If the IPG contains a rechargeable battery, the stimulation system may further comprise an external charger capable of transcutaneously recharging the IPG via inductive energy.

Recently, there has been an interest in stimulating dorsal root ganglia (DRG) for the treatment of chronic pain. The DRG is a nodule that contains cell bodies of neurons in afferent spinal nerves, and in particular, dorsal root (DR) nerve fibers. Afferent spinal nerves provide sensory information, such as touch, pain, heat/cold, and proprietary sensation, which is propagated by action potentials that travel along the nerve fibers.

As shown in FIG. 1, a DRG 1 comprises cell bodies 2 (or somas) that include axon branches projecting to central and peripheral targets. In particular, each cell body 2 is typically connected to a stem neural axon 3 that is branched to a central neural axon 4 (i.e., a spinal nerve) that extends to the spinal cord, and a peripheral neural axon 5 that extends to a peripheral region of the body. The positioning of the cell body 2 is somewhat midway between the central neural axon 4 and the peripheral neural axon 5, and thus, may be called "pseudounipolar."

Traditionally, a cell soma provides metabolic support, but DRG soma are known to undergo subthreshold depolarization when neighbor soma are invaded with afferent spikes. This means that some degree of cross-talk between the cell bodies can occur in the DRG. In healthy DRG, these interactions tend to be causal, in that regular afferent activity will generate subthreshold oscillations and some spiking while the afferent signaling is present, but rarely when sensory neurons are quiet. In pathological states, such as those following nerve injury or trauma, it is believed that the DRG soma become hyperactive, such that they generate enhanced periodic subthreshold membrane oscillations, often independent of afferent activity. In the hyperactive state, the soma have increased metabolic needs, and these needs may lead to oxygen debt and reduced mitochrondrial performance with the sensory neurons. This, in turn, can lead to ectopic electrical spiking within the sensory neurons. The action potentials resulting from the ectopic electrical spiking then feed into the dorsal horn laminae and are believed to hypersensitize these neural structures. This hypersensitization may then lead to chronic pain.

It is known to electrically stimulate the DRG to treat chronic pain. However, stimulating only the DRG may have limited effects in treating chronic pain.

There, thus, remains a need to provide a more effect technique for treating chronic pain.

SUMMARY OF THE INVENTION

In accordance with the present inventions, a method of treating a patient with an ailment (e.g., pain) is provided. The method comprises delivering first energy to a dorsal root ganglia (DRG), thereby modulating the DRG, and delivering second energy to at least one of a central neural axon extending from the DRG and a peripheral neural axon extending from the DRG, thereby modulating the at least one of the central neural axon and the peripheral neural axon. The first energy and second energy may be epidurally delivered. In one method, both the first energy and the second energy are electrical energy, although other types of neuromodulation energy, such as low-level laser energy may be used. In another method, the first electrical energy has a first frequency and the second electrical energy has a second frequency different from the first frequency. For example, the first frequency may be greater than 500 Hz, and the second frequency is equal to or less than 500 Hz, or vice versa. The first energy and the second energy may be delivered form the same neuromodulation lead. In an optional method, the second energy is delivered to one of the central neural axon and the peripheral neural axon, and third energy is delivered to the central neural axon.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 2:
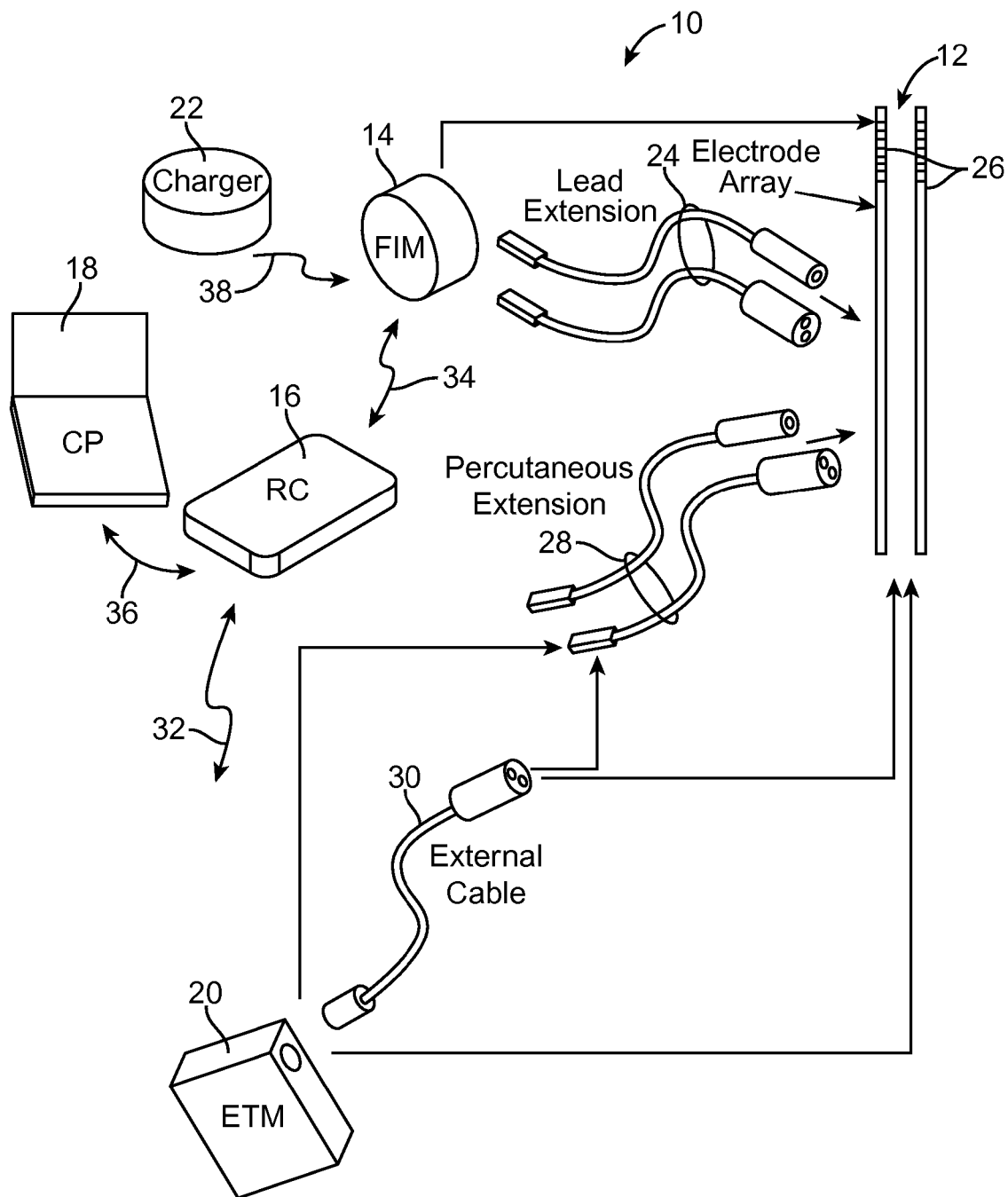
FIG. 2 is plan view of one embodiment of a neuromodulation system arranged in accordance with the present inventions.

Turning first to FIG. 2, an exemplary neuromodulation system 10 is used to modulate the dorsal root ganglion (DRG) and surrounding neural structures. The system 10 generally includes a plurality of implantable neuromodulation leads 12, a fully implantable modulator (FIM) 14, an external control device in the form of a remote controller (RC) 16, a clinician's programmer (CP) 18, an external trial modulator (ETM) 20, and an external charger 22.

The FIM 14 is physically connected via one or more lead extensions 24 to the neuromodulation leads 12, which carry a plurality of electrodes 26. Although two neuromodulation leads 12 are illustrated, it should be appreciated that less or more neuromodulation leads 12 can be provided. As will be described in further detail below, the FIM 14 includes circuitry that delivers appropriate electrical energy to the electrodes 26 in accordance with a set of neuromodulation parameters. In alternative embodiments, the energy delivered by the FIM 14 will be low-level laser energy, as described in U.S. Provisional Patent Application Ser. No. 61/652,093, entitled "Low-Level Laser Therapy, or a combination of electrical energy and low-level laser energy, as described in U.S. Provisional Patent Application Ser. No. 61/652,100, entitled "Combination Electrical Stimulation and Low-Level Laser Therapy, which are expressly incorporated herein by reference.

The ETM 20 may also be physically connected via one or more lead extensions 28 and/or one or more external cables 30 to the neuromodulation leads 12. The ETM 20, which has similar circuitry as that of the FIM 14, also delivers the electrical energy (and alternatively, low-level laser energy) to the electrodes 26 in accordance with a set of neuromodulation parameters. The major difference between the ETM 20 and the FIM 14 is that the ETM 20 is a non-implantable device that is used on a trial basis after the neuromodulation leads 12 have been implanted and prior to implantation of the FIM 14, to test the responsiveness of the neuromodulation that is to be provided. Thus, any functions described herein with respect to the FIM 14 can likewise be performed with respect to the ETM 20.

The RC 16 may be used to telemetrically control the ETM 20 via a bi-directional RF communications link 32. Once the FIM 14 and neuromodulation leads 12 are implanted, the RC 16 may be used to telemetrically control the FIM 14 via a bi-directional RF communications link 34. Such control allows the FIM 14 to be turned on or off and to be programmed with different neuromodulation parameter sets. The FIM 14 may also be operated to modify the programmed neuromodulation parameters to actively control the characteristics of the electrical energy output by the FIM 14 to the electrodes 26.

The CP 18 provides clinician detailed neuromodulation parameters for programming the FIM 14 and ETM 20 in the operating room and in follow-up sessions. The CP 18 may perform this function by indirectly communicating with the FIM 14 or ETM 20, through the RC 16, via an IR communications link 36. Alternatively, the CP 18 may directly communicate with the FIM 14 or ETM 20 via an RF communications link (not shown). The clinician detailed neuromodulation parameters provided by the CP 18 are also used to program the RC 16, so that the neuromodulation parameters can be subsequently modified by operation of the RC 16 in a stand-alone mode (i.e., without the assistance of the CP 18). The external charger 22 is a portable device used to transcutaneously charge the FIM 14 via an inductive link 38. Once the FIM 14 has been programmed, and its power source has been charged by the external charger 22 or otherwise replenished, the FIM 14 may function as programmed without the RC 16 or CP 18 being present.

For purposes of brevity, the details of the ETM 20 and external charger 22 will not be described herein. Details of exemplary embodiments of these devices are disclosed in U.S. Pat. No. 6,895,280, which is expressly incorporated herein by reference.

Figure 3:
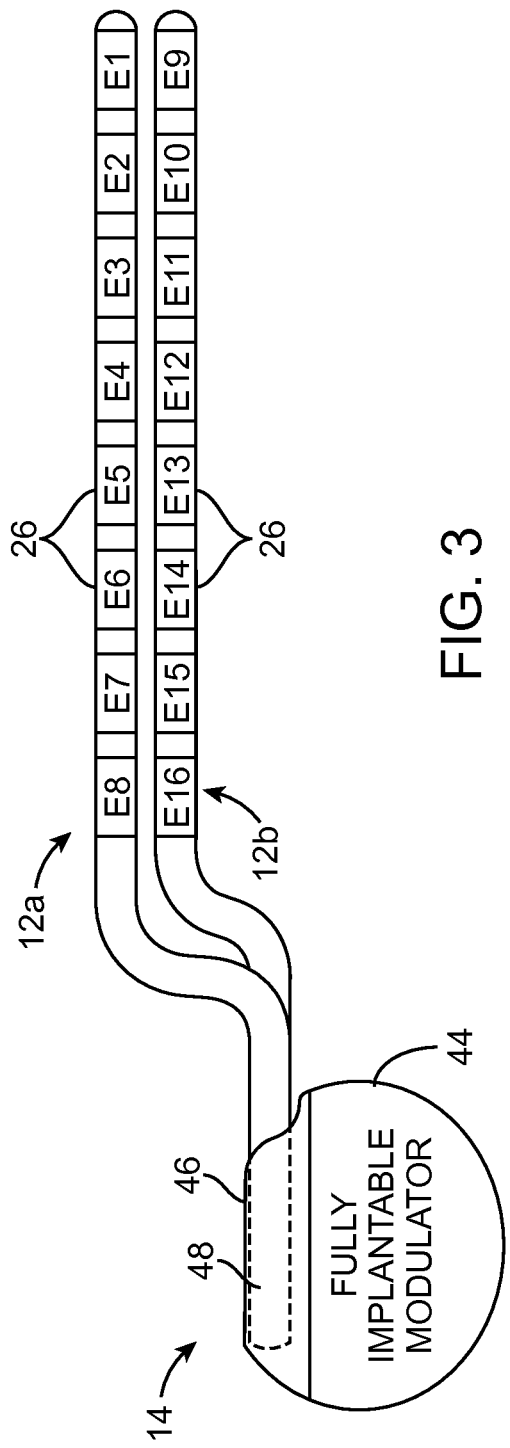
FIG. 3 is a plan view of a fully implantable modulator (FIM) and neuromodulation leads used in the neuromodulation stimulation system of FIG. 2.

Referring now to FIG. 3, the features of the neuromodulation leads 12 and the FIM 14 will be briefly described. One of the neuromodulation leads 12a has eight electrodes 26 (labeled E1-E8), and the other neuromodulation lead 12b has eight electrodes 26 (labeled E9-E16). In an alternative embodiment, the electrodes 26 may be segmented, such as those described in U.S. patent application Ser. No. 13/212,063, entitled "User Interface for Segmented Neuromodulation Leads," which is expressly incorporated herein by reference. The actual number and shape of leads and electrodes will, of course, vary according to the intended application. In alternative embodiments, the optical neuromodulation or hybrid electrical/optical neuromodulation leads can be used, the details of which are described in U.S. Provisional Patent Application Ser. No. 61/652,093, entitled "Low-Level Laser Therapy, or a combination of electrical energy and low-level laser energy, as described in U.S. Provisional Patent Application Ser. No. 61/652,100, entitled "Combination Electrical Stimulation and Low-Level Laser Therapy, which have previously been incorporated herein by reference. Further details discussing various leads designed specifically to modulate the DRG and techniques for introducing the leads adjacent the DRG and described in U.S. Provisional Patent Application Ser. No. 61/651,815, entitled "Percutaneous Implantation of an Electrical Stimulation Lead for Stimulating Dorsal Root Ganglion," U.S. Provisional Patent Application Ser. No. 61/651,917, entitled "Systems and Methods for Providing Electrical Stimulation of Multiple Dorsal Root Ganglia with a Single Lead," U.S. Provisional Patent Application Ser. No. 61/651,840, entitled "Systems and Methods for Electrically Stimulating Patient Tissue on or Around One or More Bony Structures," U.S. Provisional Patent Application Ser. No. 61/651,830, entitled "Distally Curved Electrical Stimulation Lead and Method of Making and Using," U.S. Provisional Patent Application Ser. No. 61/651,888, entitled "Systems and Methods for Implanting an Electrical Stimulation Lead Using a Sheath," and U.S. Provisional Patent Application Ser. No. 61/651,822, entitled "Methods for Stimulating The Dorsal Root Ganglion with a Lead Having Segmented Electrodes," all filed May 25, 2012, and all expressly incorporated herein by reference.

The FIM 14 comprises an outer case 44 for housing the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The FIM 14 further comprises a connector 46 to which the proximal ends of the stimulation leads 12 mate in a manner that electrically couples the electrodes 26 to the internal electronics (described in further detail below) within the outer case 44. To this end, the connector 46 includes one or more ports (two ports 48 for two percutaneous leads) for receiving the proximal end(s) of the neuromodulation leads 12. In the case where the lead extensions 24 are used, the ports 48 may instead receive the proximal ends of such lead extensions 24.

The FIM 14 includes a battery and pulse generation circuitry that delivers the electrical stimulation energy in the form of a pulsed electrical waveform to the electrode array 26 in accordance with a set of neuromodulation parameters programmed into the FIM 14. Such neuromodulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the FIM 14 supplies constant current or constant voltage to the electrode array 26), pulse width (measured in microseconds), and pulse rate (or frequency) (measured in pulses per second), burst rate (measured as the neuromodulation on duration X and neuromodulation off duration Y), and pulse shape.

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the FIM 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, the FIM 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than having a fully contained FIM, the neuromodulation system 10 may alternatively utilize an implantable receiver-modulator (not shown) connected to the neuromodulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-modulator. The implanted receiver-modulator receives the signal and generates the neuromodulation energy in accordance with the control signals.

Figure 4:
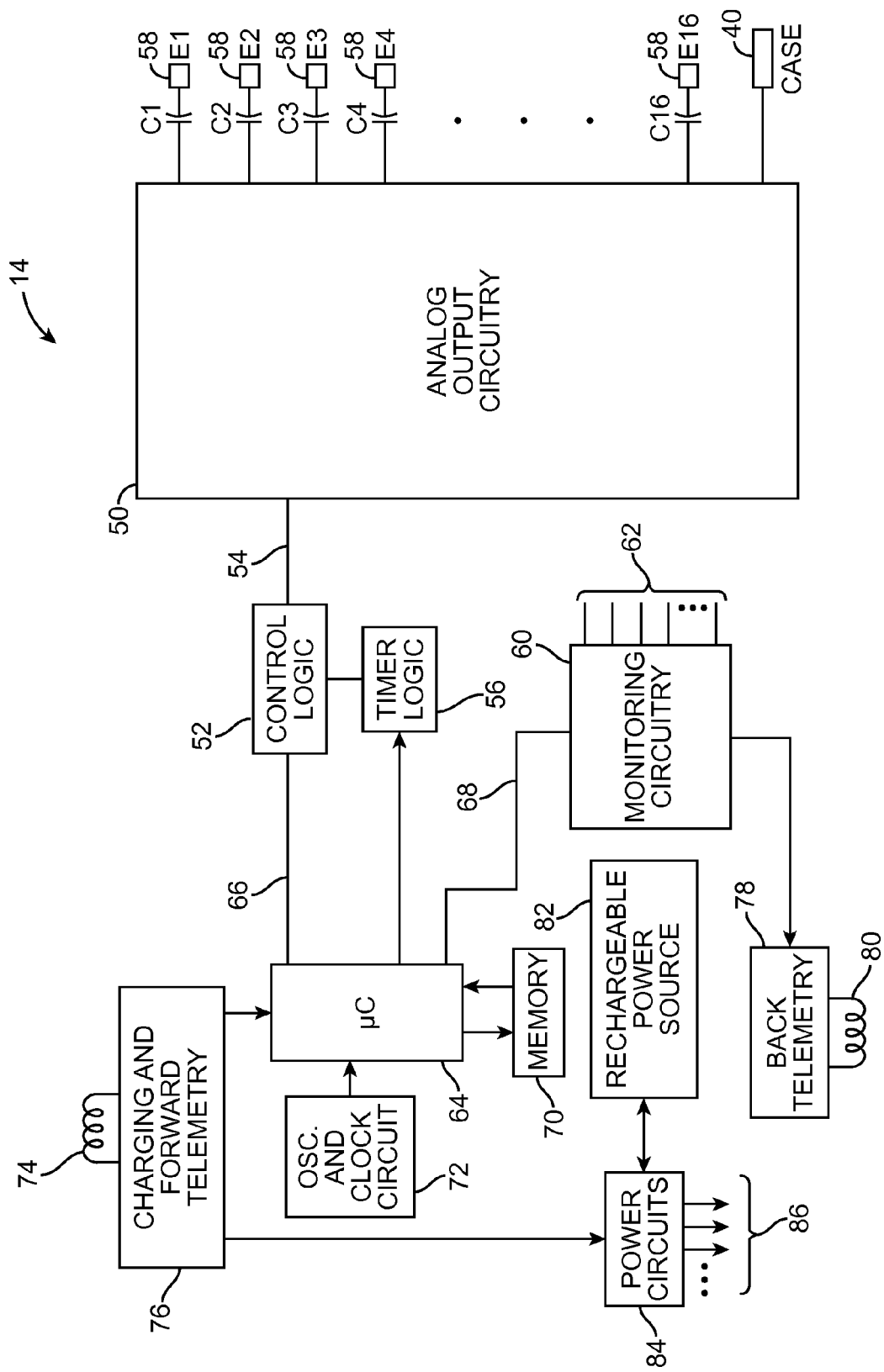
FIG. 4 is a block diagram of the internal components of an FIM used in the neuromodulation system of FIG. 2.

Turning next to FIG. 4, the main internal components of the FIM 14 will now be described. The FIM 14 includes analog output circuitry 50 configured for generating electrical neuromodulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 µs. The neuromodulation energy generated by the analog output circuitry 50 is output via capacitors C1-C16 to electrical terminals 58 corresponding to the electrodes 26. The analog output circuitry 50 may either comprise independently controlled current sources for providing electrical pulses of a specified and known amperage to or from the electrodes 26, or independently controlled voltage sources for providing electrical pulses of a specified and known voltage at the electrodes 26. The analog output circuitry 50 may optionally generate high frequency blocking electrical energy as described in U.S. patent application Ser. No. 12/819,107, entitled "Spatially Selective Nerve Stimulation in High-Frequency Nerve Conduction Block and Recruitment," and U.S. Provisional Patent Application Ser. No. 61/646,773, entitled "System and Method for Shaped Phased Current Delivery," and U.S. Provisional Patent Application Ser. No. 61/646,773, entitled "System and Method for Shaped Phased Current Delivery," which are expressly incorporated herein by reference. The analog output circuitry 50 may also optionally generate optical neuromodulation energy using any conventional miniaturized laser generation device.

Any of the N electrodes may be assigned to up to k possible groups or "channels." In one embodiment, k may equal four. The channel identifies which electrodes are selected to synchronously source or sink current to create an electric field in the tissue to be stimulated. Amplitudes and polarities of electrodes on a channel may vary, e.g., as controlled by the RC 16 (shown in FIG. 2). External programming software in the CP 18 (shown in FIG. 2) is typically used to set neuromodulation parameters including electrode polarity, amplitude, pulse rate and pulse duration for the electrodes of a given channel, among other possible programmable features. As will be discussed in further detail below, the pulse rate can be selected to be different for each of the k channels.

The N programmable electrodes can be programmed to have a positive (sourcing current), negative (sinking current), or off (no current) polarity in any of the k channels. Moreover, each of the N electrodes can operate in a multipolar (e.g., bipolar) mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode may be programmed to one of several discrete current levels, e.g., between 0 to 10 mA in steps of 0.1 mA. Also, the pulse duration of the current pulses is preferably adjustable in convenient increments, e.g., from 0 to 1 milliseconds (ms) in increments of 10 microseconds (µs). Similarly, the pulse rate is preferably adjustable within acceptable limits, e.g., from 0 to 50,000 pulses per second (pps). Other programmable features can include slow start/end ramping, burst stimulation cycling (on for X time, off for Y time), and interphase.

The operation of this analog output circuitry 50, including alternative embodiments of suitable output circuitry for performing the same function of generating stimulation pulses of a prescribed amplitude and duration, is described more fully in U.S. Pat. Nos. 6,516,227 and 6,993,384, which are expressly incorporated herein by reference.

The FIM 14 further comprises monitoring circuitry 60 for monitoring the status of various nodes or other points 60 throughout the FIM 14, e.g., power supply voltages, temperature, battery voltage, and the like. The FIM 14 further comprises processing circuitry in the form of a microcontroller (µC) 62 that controls the control logic over data bus 66, and obtains status data from the monitoring circuitry 60 via data bus 68. The FIM 14 additionally controls the timer logic 56. The FIM 14 further comprises memory 70 and oscillator and clock circuitry 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the FIM 14 in accordance with a selected operating program and neuromodulation parameters. In controlling the operation of the FIM 14, the microcontroller 64 is able to individually generate a train of stimulus pulses at the electrodes 26 using the analog output circuitry 60, in combination with the control logic 52 and timer logic 56, thereby allowing each electrode 26 to be paired or grouped with other electrodes 26, including the monopolar case electrode. In accordance with neuromodulation parameters stored within the memory 70, the microcontroller 64 may control the polarity, amplitude, rate, pulse duration and channel through which the current stimulus pulses are provided. The microcontroller 64 also facilitates the storage of electrical parameter data (or other parameter data) measured by the monitoring circuitry 60 within memory 70, and also provides any computational capability needed to analyze the raw electrical parameter data obtained from the monitoring circuitry 60 and compute numerical values from such raw electrical parameter data.

The FIM 14 further comprises an alternating current (AC) receiving coil 74 for receiving programming data (e.g., the operating program and/or neuromodulation parameters) from the RC 16 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the FIM 14.

The FIM 14 further comprises back telemetry circuitry 78 and an alternating current (AC) transmission coil 80 for sending informational data sensed through the monitoring circuitry 60 to the RC 16. The back telemetry features of the FIM 14 also allow its status to be checked. For example, when the RC 16 initiates a programming session with the FIM 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16, all programmable settings stored within the FIM 14 may be uploaded to the RC 16.

The FIM 14 further comprises a rechargeable power source 82 and power circuits 84 for providing the operating power to the FIM 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the FIM 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, the external charger 22 (shown in FIG. 2), which generates the AC magnetic field, is placed against, or otherwise adjacent, to the patient's skin over the implanted FIM 14. The AC magnetic field emitted by the external charger 22 induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external charger 22, it should be appreciated that the AC receiving coil 74 can be arranged as a dedicated charging coil, while another coil, such as coil 80, can be used for bi-directional telemetry.

It should be noted that the diagram of FIG. 4 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the DBS system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
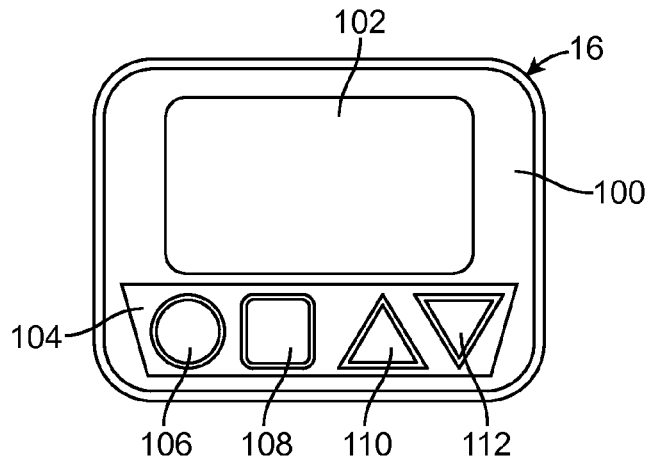
FIG. 5 is front view of a remote control (RC) used in the neuromodulation system of FIG. 2.

Referring now to FIG. 5, one exemplary embodiment of an RC 16 will now be described. As previously discussed, the RC 16 is capable of communicating with the FIM 14 or CP 18. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the FIM 14 to be turned ON and OFF, provide for the adjustment or setting of neuromodulation parameters within the FIM 14, and provide for selection between screens.

In the illustrated embodiment, the button 106 serves as an ON/OFF button that can be actuated to turn the FIM 14 ON and OFF. The button 108 serves as a select button that allows the RC 106 to switch between screen displays and/or parameters. The buttons 110 and 112 serve as up/down buttons that can be actuated to increase or decrease any of neuromodulation parameters of the electrical neuromodulation energy generated by the FIM 14, including pulse amplitude, pulse width, and pulse rate.

Figure 6:
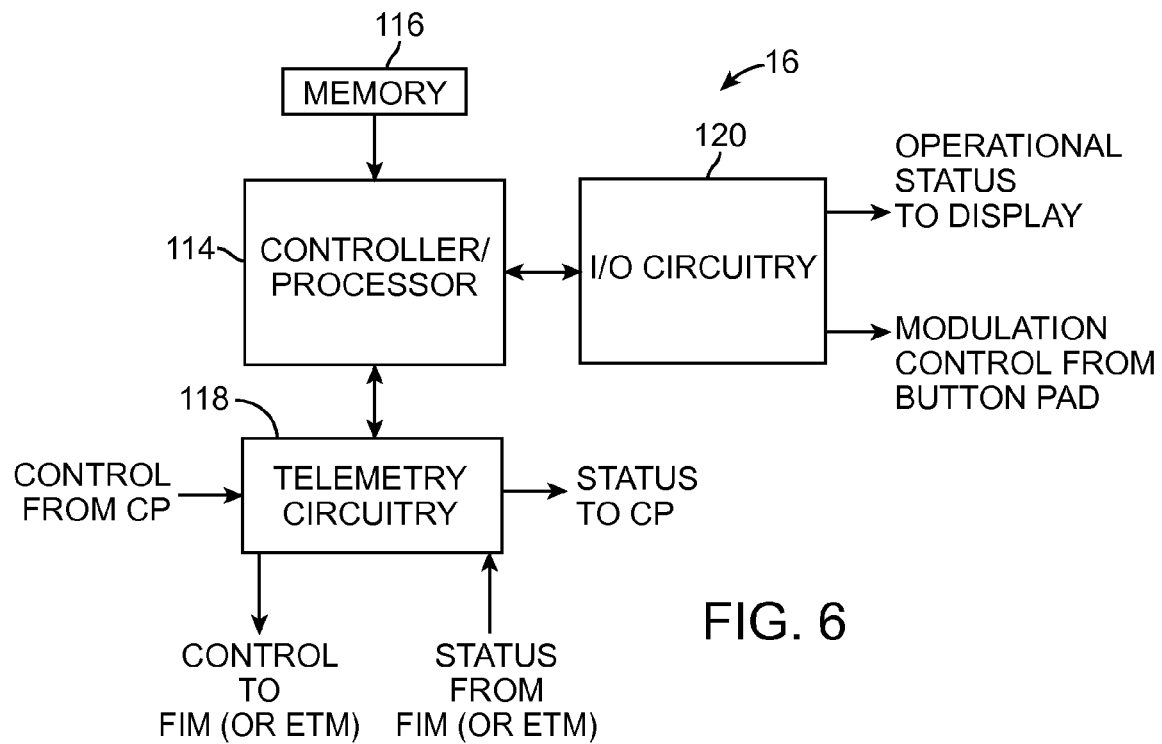
FIG. 6 is a block diagram of the internal components of the RC of FIG. 5.

Referring to FIG. 6, the internal components of an exemplary RC 16 will now be described. The RC 16 generally includes a controller/processor 114 (e.g., a microcontroller), memory 116 that stores an operating program for execution by the controller/processor 114, and telemetry circuitry 118 for transmitting control data (including neuromodulation parameters and requests to provide status information) to the FIM 14 and receiving status information (including the measured electrical data) from the FIM 14 via link 34 (or link 32) (shown in FIG. 2), as well as receiving the control data from the CP 18 and transmitting the status data to the CP 18 via link 36 (shown in FIG. 2). The RC 16 further includes input/output circuitry 120 for receiving stimulation control signals from the button pad 104 and transmitting status information to the display screen 102 (shown in FIG. 5). Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired neuromodulation parameters to be programmed into the FIM 14, as well as the RC 16. Thus, modification of the neuromodulation parameters in the programmable memory of the FIM 14 after implantation is performed by a clinician using the CP 18, which can directly communicate with the FIM 14 or indirectly communicate with the FIM 14 via the RC 16. That is, the CP 18 can be used by the physician or clinician to modify operating parameters of the electrode array 26 near the DRG.

Figure 8:
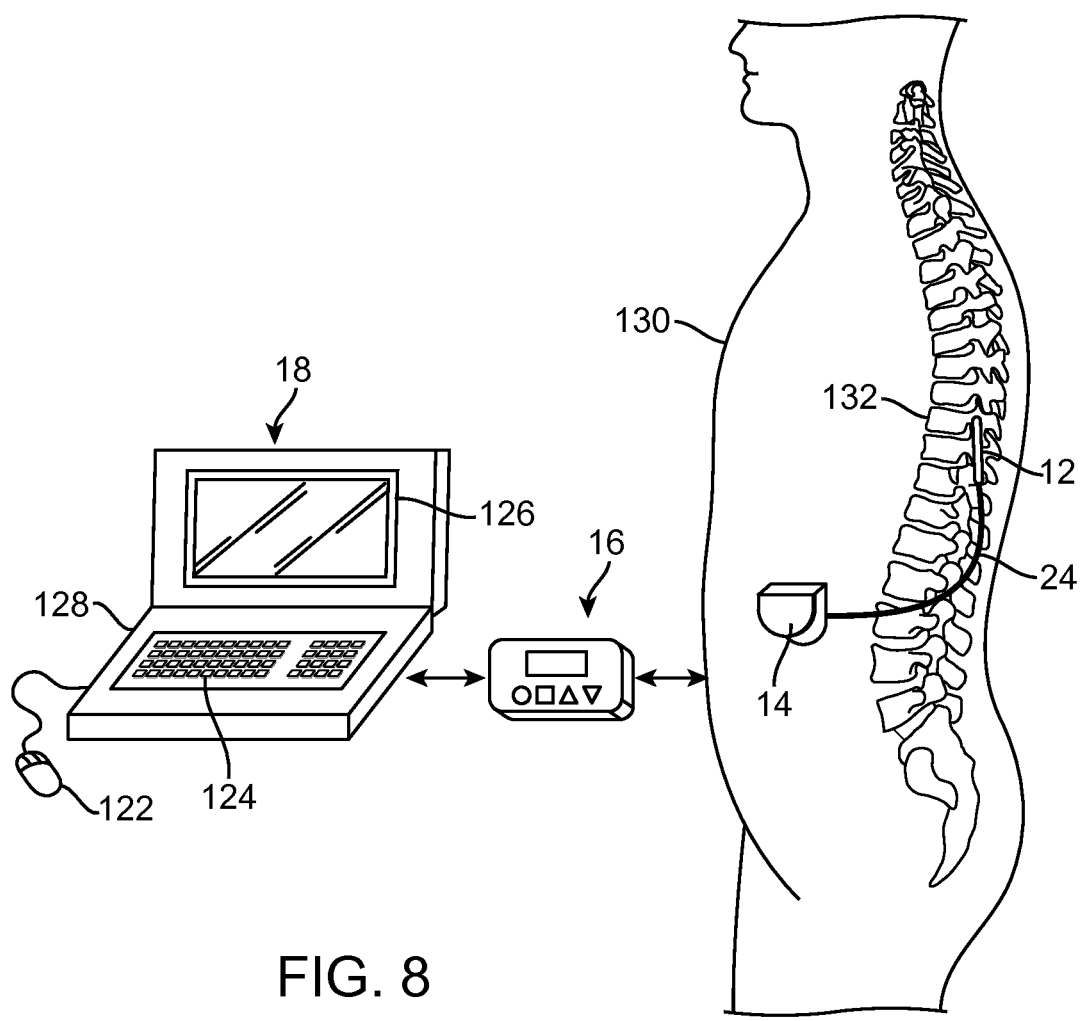
FIG. 8 is a plan view of the neuromodulation system of FIG. 2 in use within the spinal column a patient for treating chronic pain.

As shown in FIG. 8, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the FIM 14 to allow the optimum neuromodulation parameters to be determined based on patient feedback and for subsequently programming the FIM 14 with the optimum neuromodulation parameters.

To allow the clinician to perform these functions, the CP 18 includes a mouse 122, a keyboard 124, and a programming display screen 126 housed in a case 128. It is to be understood that in addition to, or in lieu of, the mouse 122, other directional programming devices may be used, such as a joystick, or directional keys included as part of the keys assigned to the keyboard 124.

Figure 1:
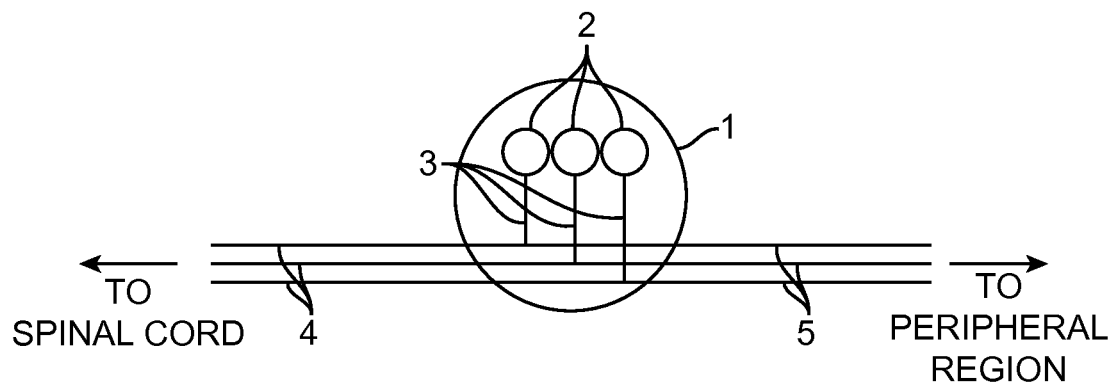
FIG. 1 is a prior art plan view of a dorsal root ganglion (DRG) and surrounding neural structures.
Figure 7:
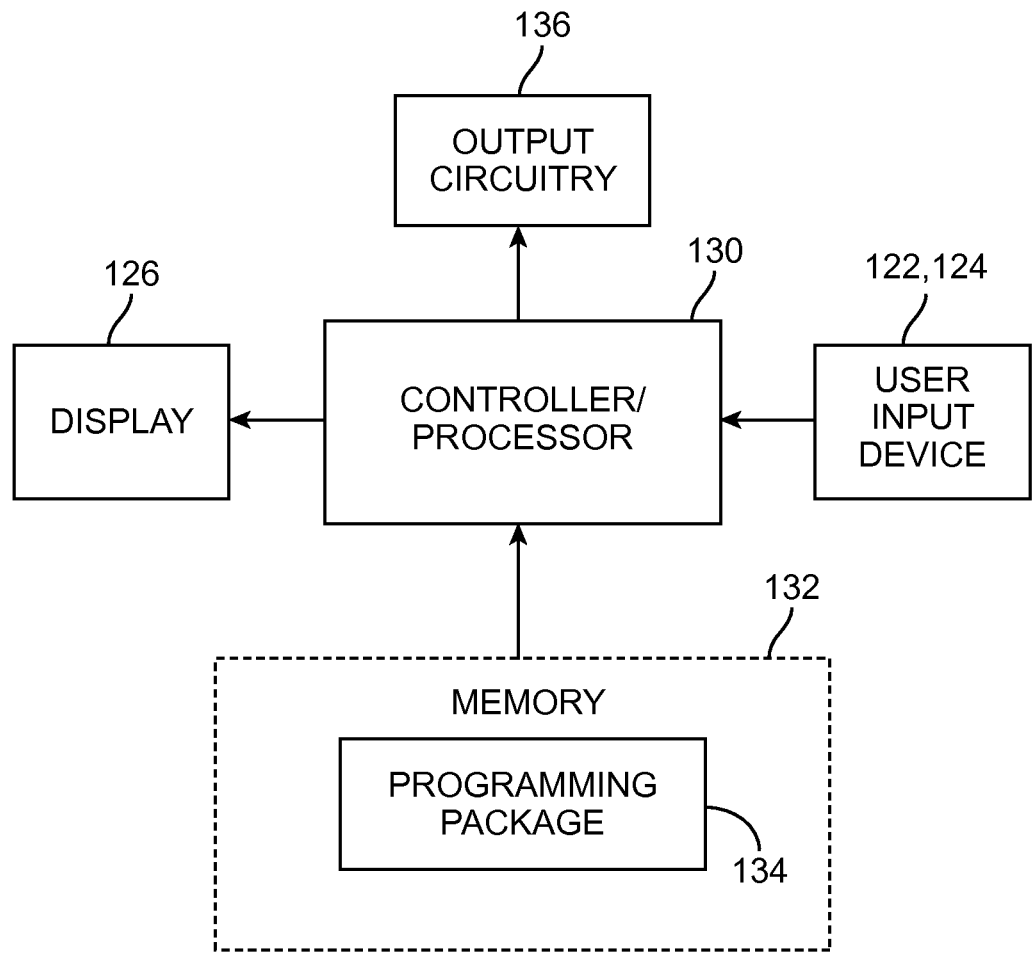
FIG. 7 is a block diagram of the internal components of a clinician's programmer (CP) used in the neuromodulation system of FIG. 2.

As shown in FIG. 7, the CP 18 generally includes a controller/processor 130 (e.g., a central processor unit (CPU)) and memory 132 that stores a stimulation programming package 134, which can be executed by the controller/processor 130 to allow a clinician to program the FIM 14 and RC 16. The CP 18 further includes telemetry circuitry 136 for downloading neuromodulation parameters to the RC 16 and uploading neuromodulation parameters already stored in the memory 116 of the RC 16 via link 36 (shown in FIG. 1). The telemetry circuitry 136 is also configured for transmitting the control data (including neuromodulation parameters and requests to provide status information) to the FIM 14 and receiving status information from the FIM 14 indirectly via the RC 16.

Execution of the programming package 134 by the controller/processor 130 provides a multitude of display screens (not shown) that can be navigated through via use of the mouse 122. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), define the configuration and orientation of the leads, initiate and control the electrical stimulation energy output by the leads 12, and select and program the FIM 14 with neuromodulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neuromodulation Electrodes," which are expressly incorporated herein by reference.

Figure 9:
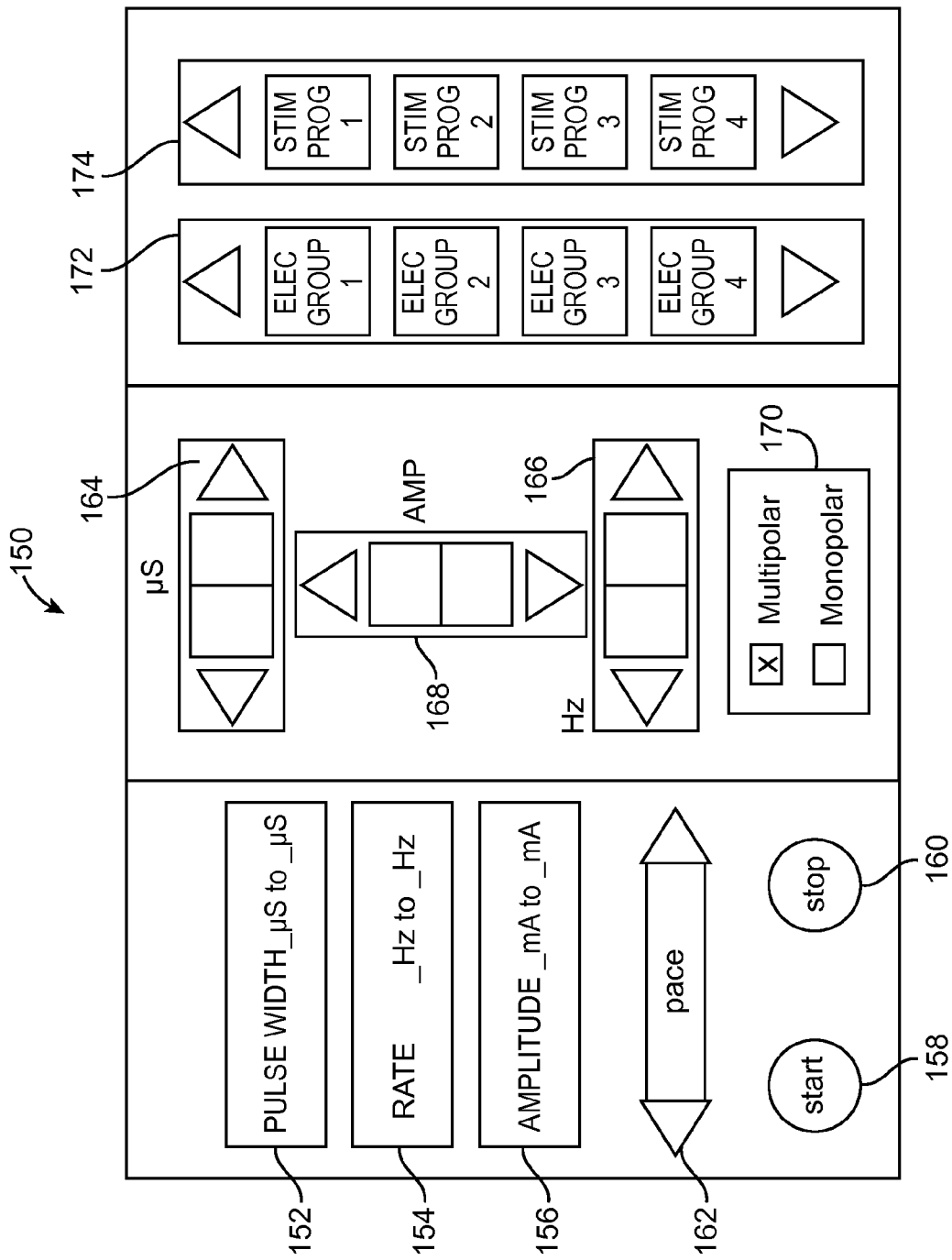
FIG. 9 is a plan view of a one embodiment of a programming screen that can be generated by the CP of FIG. 8.

An example of a programming screen 150 that can be generated by the CP 18 is shown in FIG. 9. The programming screen 150 allows a user to perform automated neuromodulation parameter testing, manual neuromodulation parameter testing, and electrode combination selection functions.

The programming screen 150 includes various neuromodulation parameter entries that define the ranges of neuromodulation parameters to be automatically tested. In particular, the programming screen includes a pulse width entry 152 (expressed in microseconds (μs)), a pulse rate entry 154 (expressed in Hertz (Hz)), and a pulse amplitude entry 156 (expressed in milliamperes (mA)). The user may enter a "begin" value and an "end" value for each neuromodulation parameter to be automatically adjusted. The values of the pulse amplitude, pulse width, and pulse rate will be limited in accordance with the electrical neuromodulation parameter limit values stored in the FIM 14 and/or CP 18, such that the CP 18 will not allow the user to enter values outside of the allowed range. In one embodiment, only a single parameter (e.g., pulse width entry 154) is highlighted to be auto-adjusted. The programming screen 150 also includes a start button 158, which begins the automatic adjustment of the highlighted neuromodulation parameter from its "begin" value through a minimum increment to its "end" value, and a stop button 160, which halts the automatic adjustment of the highlighted neuromodulation parameter. The programming screen 150 also includes a pacing control 162, the left arrow of which can be clicked to decrease the speed of the parameter adjustment and the right arrow of which can be clicked to increase the speed of the parameter adjustment.

The programming screen 150 also includes various neuromodulation parameter controls that can be operated by the user to manually adjust neuromodulation parameters. In particular, the programming screen 150 includes a pulse width adjustment control 164 (expressed in microseconds (μs)), a pulse rate adjustment control 166 (expressed in Hertz (Hz)), and a pulse amplitude adjustment control 168 (expressed in milliamperes (mA)). Each control includes a first arrow that can be clicked to decrease the value of the respective neuromodulation parameter and a second arrow that can be clicked to increase the value of the respective neuromodulation parameter. The programming screen 150 also includes multipolar/monopolar stimulation selection control 170, which includes check boxes that can be alternately clicked by the user to provide multipolar or monopolar stimulation.

The programming screen 150 also includes an electrode group control 172 having arrows that can be clicked by the user to select one of four different electrode groups 1-4, which respectively correspond to the four k channels discussed above with respect to the FIM 14. Each of the electrode groups 1-4 can be conventionally created either manually; for example, clicking on selected electrodes of a graphical electrode array (not shown) as anodes and cathodes and defining a percentage anodic current or cathodic current for each selected electrode (e.g., turning off electrode E1 as an anode, and turning on electrode E2 as an anode, and defining an anodic current for electrode E2), or automatically; for example, by gradually shifting current between anodic ones of the electrodes and/or gradually shifting current between cathodic ones of the electrodes via a directional device, such as a joystick or mouse (e.g., shifting anodic electrical current from electrode E1 to electrode E2 in 5% increments). A set of electrical neuromodulation parameters (pulse amplitude, pulse width, and pulse rate, as defined by the manual adjust neuromodulation parameters) is associated with each electrode group.

The programming screen 150 also includes a program control 174 having arrows that can be clicked by the user to select one of four different stimulation programs 1-4. Each of the programs can be operated over four different timing channels for the respective four electrode groups defined by the electrode group control 172 and associated electrical neuromodulation parameters. As described above, although the number of programs is four and the number of electrode groups (timing channels) is four, these numbers will vary based on the type of FIM.

Having described the structure and function of the neuromodulation system 10, various techniques for using the neuromodulation system 10 to treat patients having pain, which may be chronic, will now be described. In these methods, electrical neuromodulation energy is delivered to a dorsal root ganglia (DRG), thereby modulating the DRG; as well as the surrounding neural structures, including the central neural axon extending from the DRG and/or the peripheral neural axon extending from the DRG. Modulation of the DRG and surrounding neural structures modulates the sensory information, such as pain, touch, heat, and proprietary sensation traveling through the DRG. The effect on the DRG and surrounding neural structures will depend on the frequency of the electrical neuromodulation energy. If low frequency electrical stimulation is used (500 Hz or less), the neural structure will be directly depolarized or hyperpolarized, depending on the orientation of the electrode relative to the neural structure, as well as the whether the electrical current is anodic or cathodic. This is believed to transform ectopic firing of the DRG or surrounding neural structures into a tonic firing, which may be perceived as paresthesia, or dull or no pain. If high frequency electrical stimulation is used (greater than 500 Hz), the neural structure may be preconditioned to block action potential initiation and/or change the interpulse interval between successive action potentials. In any event, the electrical energy modulates the electrical properties of the neural structure, thereby manipulating the sensory information.

Figure 10:
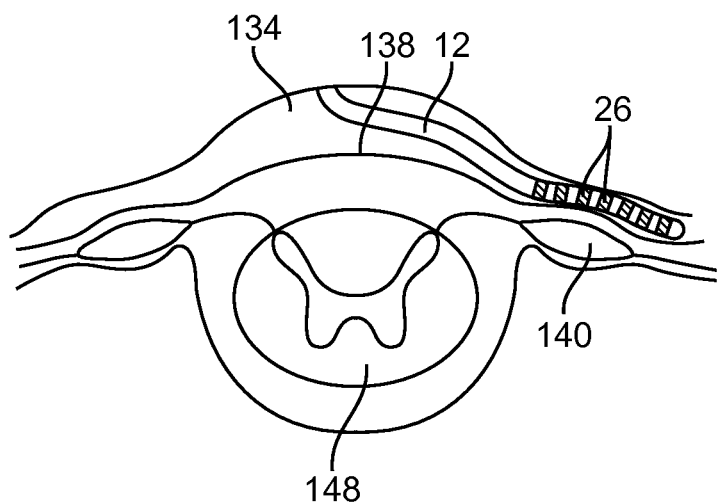
FIG. 10 is a cross-sectional view showing the use of a neuromodulation lead in modulating a dorsal root ganglion (DRG)

In one method for treating chronic pain, the DRG and surrounding neural structures may be modulated by implanting a neuromodulation lead 12 within the spinal column 132 of a patient 130, as shown in FIG. 8. As shown in FIG. 10, the preferred placement of the neuromodulation lead 12 is in the epidural space 134 of the patient 100. The neuromodulation lead 12 may be located in the foramen 136 that extends from the epidural space 134 over the dura 138 covering the DRG 140. In this manner, electrical neuromodulation energy can be conveniently delivered to the DRG 140 and surrounding neural structures. The percutaneous neuromodulation lead 12 can conventionally be introduced, with the aid of fluoroscopy, into the epidural space 134 above the spinal cord 148 through a Touhy-like needle, which passes through the skin, between the desired vertebrae, and into the epidural space 134 above the dura 138. In many cases, a stylet, such as a metallic wire, is inserted into a lumen running through the center of the neuromodulation lead 12 to aid in insertion of the lead through the needle and into the epidural space 134. The neuromodulation lead 12 may then be introduced into the foramen 136 from the epidural space 134. The stylet gives the lead rigidity during positioning, and once the neuromodulation lead 12 is positioned, the stylet can be removed after which the lead becomes flaccid.

After proper placement of the neuromodulation lead 12 at the target area of the spinal column 102, the neuromodulation lead 12 is anchored in place to prevent movement of the neuromodulation lead 12. To facilitate the location of the FIM 14 away from the exit point of the neuromodulation lead 12 implanted within the spinal column 102, a lead extension 24 may be used. Whether a lead extension is used or not, the proximal end of the neuromodulation lead 12 exiting the spinal column 102 is passed through one or more tunnels (not shown) subcutaneously formed along the torso of the patient 100 to a subcutaneous pocket (typically made in the patient's abdominal or buttock area) where the FIM 14 is implanted. The FIM 14 may, of course, also be implanted in other locations of the patient's body. A subcutaneous tunnel can be formed using a tunneling tool over which a tunneling straw may be threaded. The tunneling tool can be removed, the neuromodulation lead 12 threaded through the tunneling straw, and then the tunneling straw removed from the tunnel while maintaining the neuromodulation lead 12 in place within the tunnel.

The neuromodulation lead 12 is then connected directly to the FIM 14 by inserting the proximal end of the neuromodulation lead 12 within the connector port located on the connector 42 of the FIM 14 or connected to lead extension 24, which is then inserted into the connector port of the FIM 14. The FIM 14 can then be operated to generate the electrical energy, which is delivered, through selected ones of the electrodes E1-E8 to the targeted tissue. As there shown, the CP 18 communicates with the FIM 14 via the RC 16, thereby providing a means to control and reprogram the FIM 14.

Figure 11:
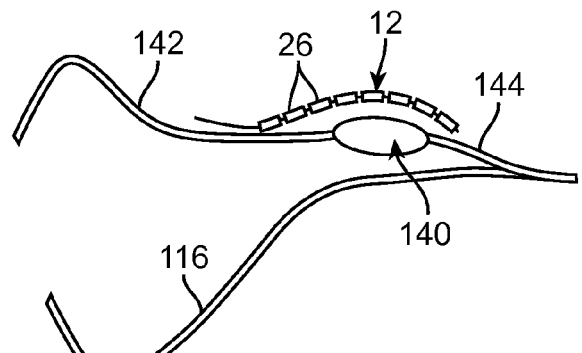
FIG. 11 is a plan view of a neuromodulation lead located above the DRG and surrounding neural structures.

Referring to FIG. 11, a neuromodulation lead 12 is shown extending along the DRG 140 and the portions of the central neural axon 142 (as part of the dorsal root (DR) and the peripheral neural axon 144 extending from the DRG 140. For purposes of context, the ventral root (VR) 116 is also shown. The electrodes 26 of the neuromodulation lead 12 may be topologically divided into groups in accordance with which electrodes 26 are located over which of the DRG 140, central neural axon 142, and peripheral neural axon 144. That is, electrodes 26 located over the DRG 140 can be included within one electrode group, electrodes 26 located over the central neural axon 142 can be included within another electrode group, and electrodes 26 located over the peripheral neural axon 144 can be included within still another electrode group. The electrode groups can then be combined into a neuromodulation program. The location and grouping of the electrodes 26 may depend on the source of the pain.

Figure 12A:
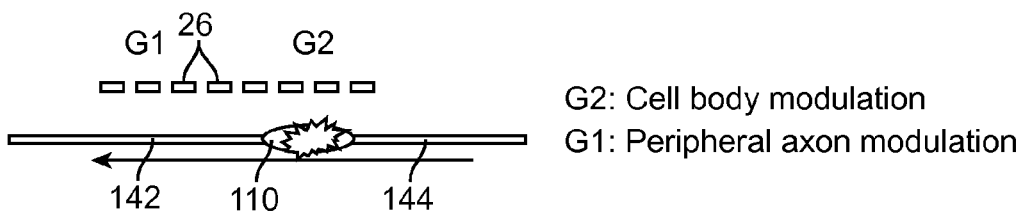
FIGS. 12a-12c are plan views showing the possible sources of pain and the respective electrode grouping that can be used to treat the pain.
Figure 13A:
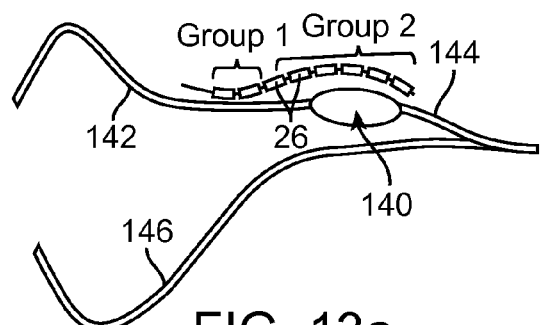
FIG. 13a-13c are plan views showing various electrode groupings used to treat the pain illustrated in FIGS. 12a-12c and the respective low/high frequency tables.

For example, if the source of pain resides only in the DRG 140, as illustrated in FIG. 12a, electrical energy can be delivered to the both the DRG 140 and the central neural axon 142. To this end, the electrodes 26 can be divided into "Group 1" located over the central neural axon 142, and "Group 2" located over the DRG 140, as shown in FIG. 13a. Different combinations of low frequency electrical energy and high frequency electrical energy can be conveyed from the Group 1 electrodes and Group 2 electrodes to the respective central neural axon 142 and DRG 140. For example, four different combinations can be made as follows: Combination 1 (low frequency electrical energy for Group 1 and low frequency electrical energy for Group 2); Combination 2 (low frequency electrical energy for Group 1 and high frequency electrical energy for Group 2); Combination 3 (high frequency electrical energy for Group 1 and high frequency electrical energy for Group 2); and Combination 4 (high frequency electrical energy for Group 1 and low frequency electrical energy for Group 2).

Figure 12B:
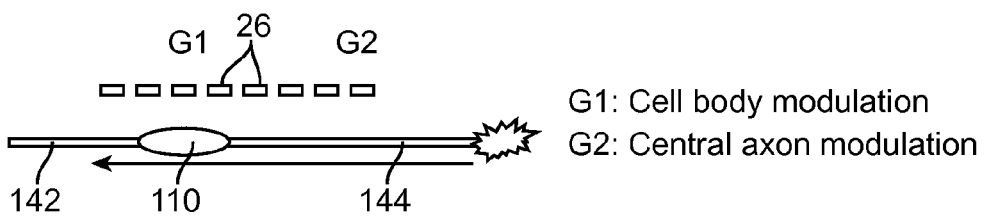
Figure 13B:
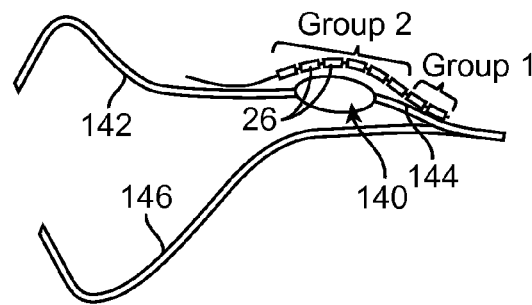

As another example, if the source of pain resides only in the peripheral neural axon 144, as illustrated in FIG. 12b, electrical energy can be delivered to the both the DRG 140 and the peripheral neural axon 144. To this end, the electrodes 26 can be divided into "Group 1" located over the peripheral neural axon 144, and "Group 2" located over the DRG 140, as shown in FIG. 13b. Different combinations of low frequency electrical energy and high frequency electrical energy can be conveyed from the Group 1 electrodes and Group 2 electrodes to the respective peripheral neural axon 144 and DRG 140. For example, four different combinations can be made as follows: Combination 1 (low frequency electrical energy for Group 1 and low frequency electrical energy for Group 2); Combination 2 (low frequency electrical energy for Group 1 and high frequency electrical energy for Group 2); Combination 3 (high frequency electrical energy for Group 1 and high frequency electrical energy for Group 2); and Combination 4 (high frequency electrical energy for Group 1 and low frequency electrical energy for Group 2).

Figure 12C:
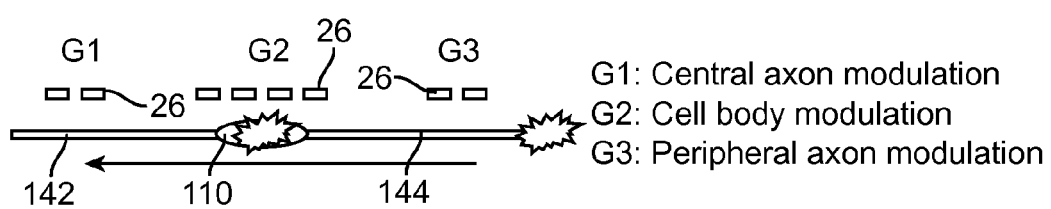
Figure 13C:
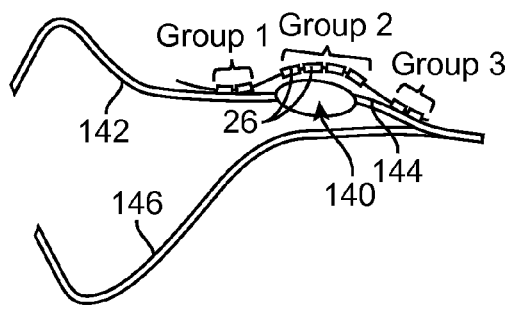

As still another example, if the source of pain resides in both the DRG 140 and the peripheral neural axon 144, as illustrated in FIG. 12c, electrical energy can be delivered to all three of the DRG 140, the central neural axon 142, and the peripheral neural axon 144. To this end, the electrodes 26 can be divided into "Group 1" located over the central neural axon 142, "Group 2" located over the DRG 140, and "Group 3 located over the peripheral neural axon 144, as shown in FIG. 13c. Different combinations of low frequency electrical energy and high frequency electrical energy can be conveyed from the Group 1 electrodes, Group 2 electrodes, and Group 3 electrodes to the central neural axon 142, DRG 140, and peripheral neural axon 144. For example, eight different combinations can be made as follows: Combination 1 (low frequency electrical energy for Group 1, low frequency electrical energy for Group 2, and high frequency electrical energy for Group 3); Combination 2 (low frequency electrical energy for Group 1, high frequency electrical energy for Group 2, and high frequency electrical energy for Group 3); Combination 3 (high frequency electrical energy for Group 1, high frequency electrical energy for Group 2, and low frequency electrical energy for Group 3); Combination 4 (high frequency electrical energy for Group 1, low frequency electrical energy for Group 2, and low frequency electrical energy for Group 3), Combination 5 (high frequency electrical energy for Group 1, low frequency electrical energy for Group 2, and high frequency electrical energy for Group 3), Combination 6 (low frequency electrical energy for Group 1, high frequency electrical energy for Group 2, and low frequency electrical energy for Group 3), Combination 7 (low frequency electrical energy for Group 1, low frequency electrical energy for Group 2, and low frequency electrical energy for Group 3), and Combination 8 (high frequency electrical energy for Group 1, high frequency electrical energy for Group 2, and high frequency electrical energy for Group 3).

Although the different combinations of electrodes have focused on frequency, it should be appreciated that other neuromodulation parameters, such as pulse width and pulse shape can be used, to make different combinations of electrodes. Furthermore, other types of neuromodulation energy may be used to make different combinations of electrodes. For Group 1 electrodes may convey electrical neuromodulation energy, while Group 2 electrodes may convey low-level laser energy, or vice versa. Different techniques for conveying low-level laser energy, alone, or in combination with electrical energy, are disclosed in U.S. Provisional Patent Application Ser. No. 61/652,093, entitled "Low-Level Laser Therapy, or a combination of electrical energy and low-level laser energy, as described in U.S. Provisional Patent Application Ser. No. 61/652,100, entitled "Combination Electrical Stimulation and Low-Level Laser Therapy, which have previously been incorporated herein by reference.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of treating a patient with an ailment, comprising:
providing an implanted neuromodulation lead comprising a plurality of electrodes, the plurality of electrodes comprising a first electrode and a second electrode spaced apart from the first electrode, wherein the first electrode is disposed over a dorsal root ganglia (DRG) and the second electrode is disposed over one of a central neural axon extending from the DRO or a peripheral neural axon extending from the DRG;
delivering first energy to the dorsal root ganglia using at least the first electrode but not the second electrode, thereby modulating the DRG; and
delivering second energy to the one of the central neural axon or the peripheral neural axon using at least the second electrode but not the first electrode, thereby modulating the one of the central neural axon or the peripheral neural axon, wherein the first energy and the second energy differ in at least one of frequency, energy type, pulse width, or pulse shape, wherein the first energy depolarizes or hyperpolarizes the DRG and the second energy blocks action potential initiation or changes an interpulse interval between action potentials in the one of the central neural axon or the peripheral neural axon.

2. The method of claim 1. wherein both the first energy and the second energy are electrical energy.

3. The method of claim 2, wherein the first electrical energy has a first frequency and the second electrical energy has a second frequency different from the first frequency.

4. The method of claim 3, wherein the first frequency is equal to or less than 500Hz, and the second frequency is greater than 500Hz.

5. The method of claim 1. wherein the second energy is delivered to one of the central neural axon or the peripheral neural axon, the method further comprising delivering third energy to the other of the central neural axon or the peripheral neural axon.

6. The method of claim 1 wherein the ailment is pain.

7. The method of claim 6, wherein the source of pain resides in the DRG and the second electrode is disposed over the central neural axon and the second energy is delivered to the central neural axon.

8. The method of claim 6, wherein the source of pain resides in the peripheral neural axon and the second electrode is disposed over the peripheral neural axon and the second energy is delivered to the peripheral neural axon.

9. The method of claim 6, wherein the source of pain resides both in the DRG and the peripheral neural axon and the second electrode is disposed over the peripheral neural axon and the second energy is delivered to the peripheral neural axon, the method further comprising delivering, third energy to the central neural axon.

10. The method of claim 5, wherein the neurostimulation lead comprises a third electrode, wherein the third electrode is disposed over the other one of the central neural axon or the peripheral neural axon, wherein the third energy is delivered using at least the third electrode but not the first and second electrodes.

11. The method of claim 10, wherein the third energy differs from both the first energy and the second energy in at least one of frequency, energy type, pulse width, or pulse shape.

12. A method of treating a patient with an ailment, comprising,:
providing an implanted neuromodulation lead comprising a plurality of electrodes, the plurality of electrodes comprising a first electrode and a second electrode spaced apart from the first electrode, wherein the first electrode is disposed over a dorsal root ganglia (DRG) and the second electrode is disposed over one of a central neural axon extending from the DRG or a peripheral neural axon extending from the DRG;
delivering first energy to the dorsal root ganglia using at least the first electrode but not the second electrode, thereby modulating the DRG: and delivering second energy to the one of the central neural axon or the peripheral neural axon using at least the second electrode but not the first electrode, thereby modulating the one of the central neural axon or the peripheral neural axon, wherein the first energy and the second energy differ in at least one of frequency, energy type, pulse width, or pulse shape, wherein the first energy blocks action potential initiation or changes an interpulse interval between action potentials in the DRG and the second energy depolarizes or hyperpolarizes the one of the central neural axon or the peripheral neural axon.

13. The method of claim 12, wherein the first energy has a first frequency and the second energy has a second frequency different from the first frequency.

14. The method of claim 13, wherein the first frequency is greater than 500Hz, and the second frequency is equal to or less than 500Hz.

15. The method of claim 12, wherein the ailment is pain.

16. The method of claim 15, wherein the source of pain resides in the DRG and the second electrode is disposed over the central neural axon and the second energy is delivered to the central neural axon.

17. The method of claim 15, wherein the source of pain resides in the peripheral neural axon and the second electrode is disposed over the peripheral neural axon and the second energy is delivered to the peripheral neural axon.

18. The method of claim 15, wherein the source of pain resides both in the DRG and the peripheral neural axon and the second electrode is disposed over the peripheral neural axon and the second energy is delivered to the peripheral neural axon, the method further comprising delivering third energy to the central neural axon.

19. The method of claim 12, wherein the second energy is delivered to one of the central neural axon or the peripheral neural axon, the method further comprising delivering third energy to the other of the central neural axon or the peripheral neural axon.

20. The method of claim 19. wherein the neurostimulation lead comprises a third electrode, wherein the third electrode is disposed over the other one of the central neural axon or the peripheral neural axon, wherein the third energy is delivered using at least the third electrode but not the first and second electrodes, wherein the third energy differs from both the first energy and the second energy in at least one of frequency, energy type, pulse width, or pulse shape.

* * * * *